United States Patent [19]
Eberhard et al.

[11] Patent Number: 4,920,491

[45] Date of Patent: Apr. 24, 1990

[54] ENHANCEMENT OF IMAGE QUALITY BY UTILIZATION OF A PRIORI INFORMATION

[75] Inventors: Jeffrey W. Eberhard; Kristina H. Hedengren, both of Schenectady, N.Y.

[73] Assignee: General Electric Company, Schenectady, N.Y.

[21] Appl. No.: 194,235

[22] Filed: May 16, 1988

[51] Int. Cl.⁵ .................... G01N 23/04; G06F 15/42
[52] U.S. Cl. ........................ 364/413.19; 364/413.14; 378/901
[58] Field of Search .................... 364/413.13, 413.14, 364/413.16, 413.2, 413.19; 378/901; 358/111

[56] References Cited

U.S. PATENT DOCUMENTS

| | | | |
|---|---|---|---|
| 4,506,327 | 3/1985 | Tam | 364/414 |
| 4,618,924 | 10/1985 | Hinds | 364/191 |

FOREIGN PATENT DOCUMENTS 2203620  10/1988  United Kingdom ........... 364/413.14

OTHER PUBLICATIONS

Tam et al., "Limited-angle... Transform Iterations", Optical Engineering, vol. 20, No. 4, pp. 586–589; Jul.-/Aug. 1981.
Tam, "Two dimensional... Plan characterization", Journal of Nondestructive Evaluation, vol. 5, No. 2, pp. 95, 106, 1985.
K. C. Tam and V. Perez-Mendez, "Tomographical Imaging with Limited-Angle Input", J. Opt. Soc. Am., 71, May 1981, 582–592.
K. C. Tam and V. Perez-Mendez, "Limits to Image Reconstruction from Restricted Angular Input", IEEE Trans. Nuci. Sci., NS-28, Feb. 1981, 179–181.
K. C. Tam, "The Use of Convex Hulls in Limited-Angle Computerized Tomography", TIS Report No. 88CRD006, Feb. 1988, General Electric Co., Corporate Research and Development, P.O. Box 8, Schenectady, NY 12301.

Primary Examiner—Jerry Smith
Assistant Examiner—Kim Thanh Tbui
Attorney, Agent, or Firm—Henry I. Steckler; James C. Davis, Jr.; Paul R. Webb, II

[57] ABSTRACT

The quality of incomplete data Non-Destructive Evaluation and Computed Tomography images is improved by incorporating a priori information into the image reconstruction and image processing to supplement the available data. The a priori information is provided by electronic models of the part derived from a solid modeler, physics of the inspection process, and outputs of touch and other sensors. Methods of improving limited-angle X-ray CT images are given. Calculated projection data in the missing angular range is provided by calculating x-ray path lengths through a solid model of the part, and x-ray attenuation from known physical parameters of the part and source. The measured and calculated projection data are combined to reconstruct the CT image. In an iterative reconstruction approach, precise boundary information from a model and calculated attenuation are information to improve the limited angle image.

10 Claims, 5 Drawing Sheets

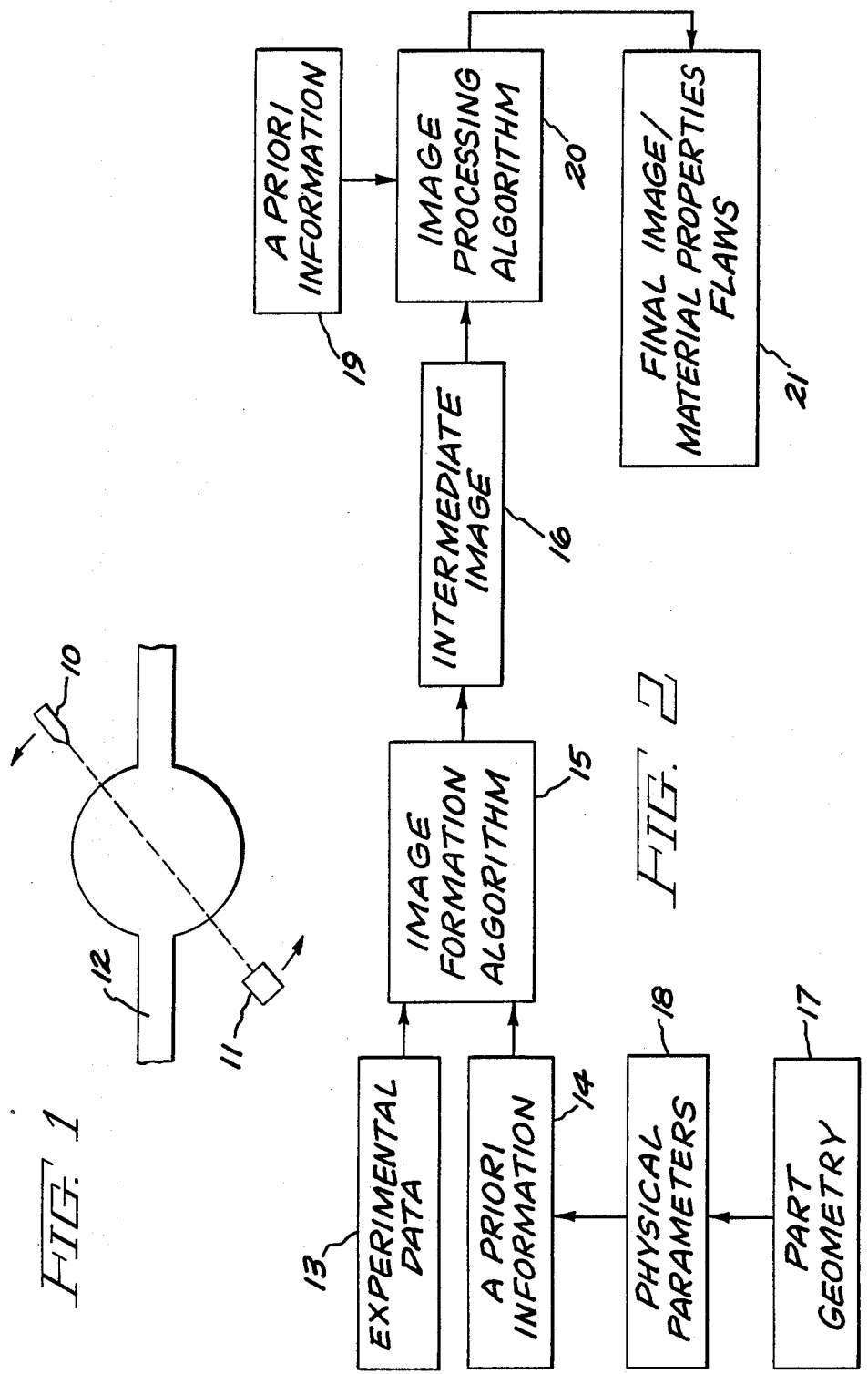

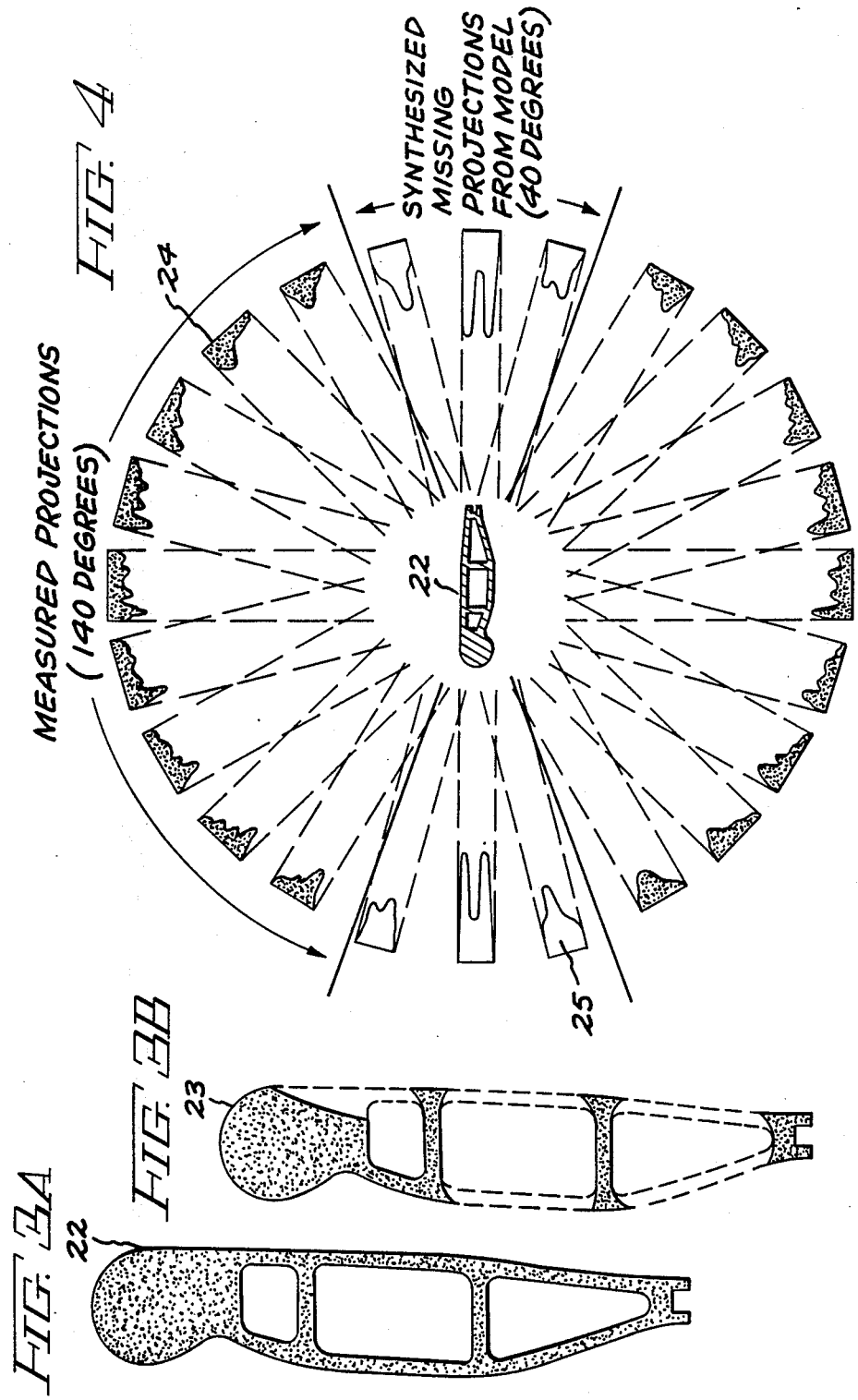

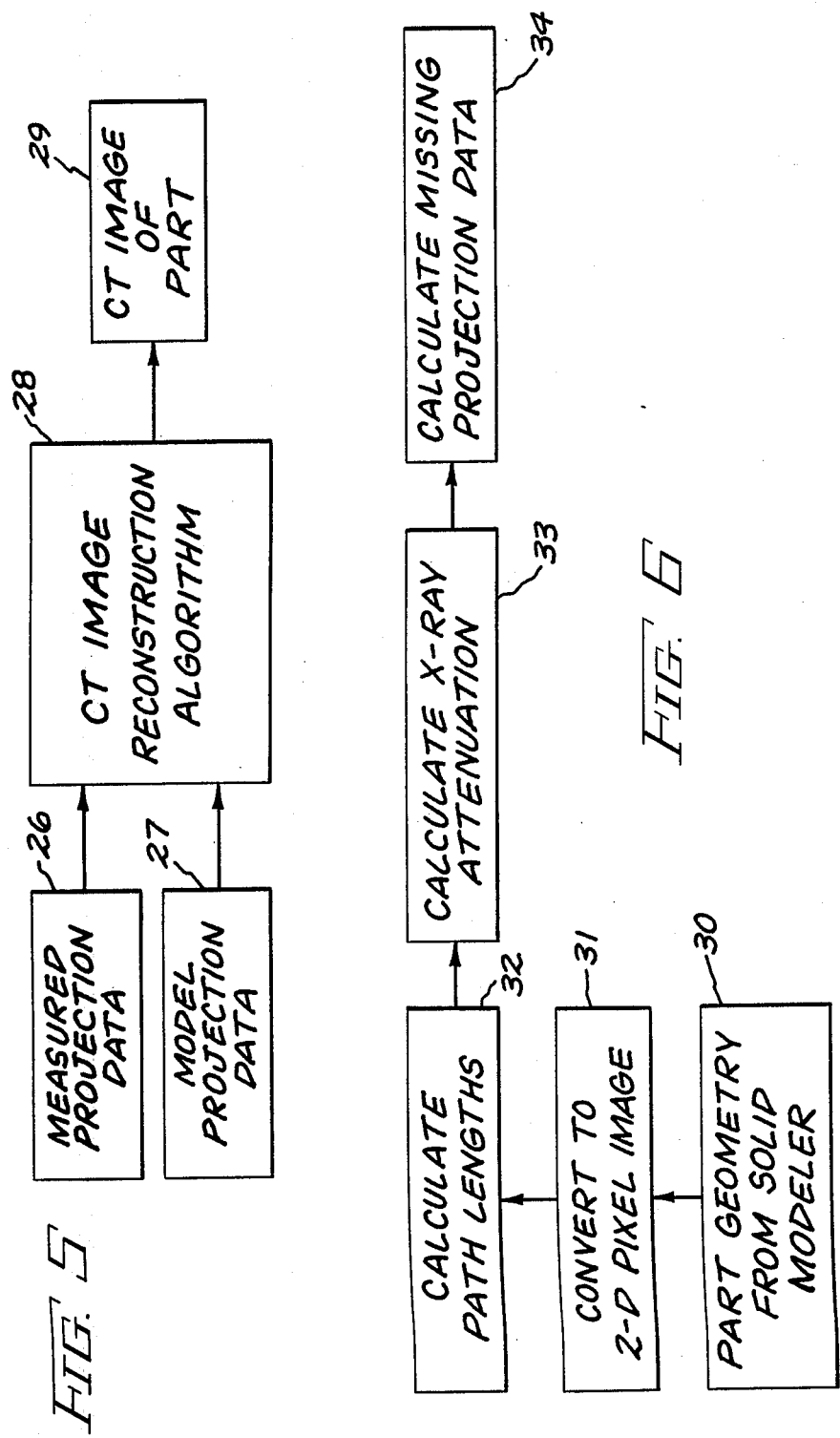

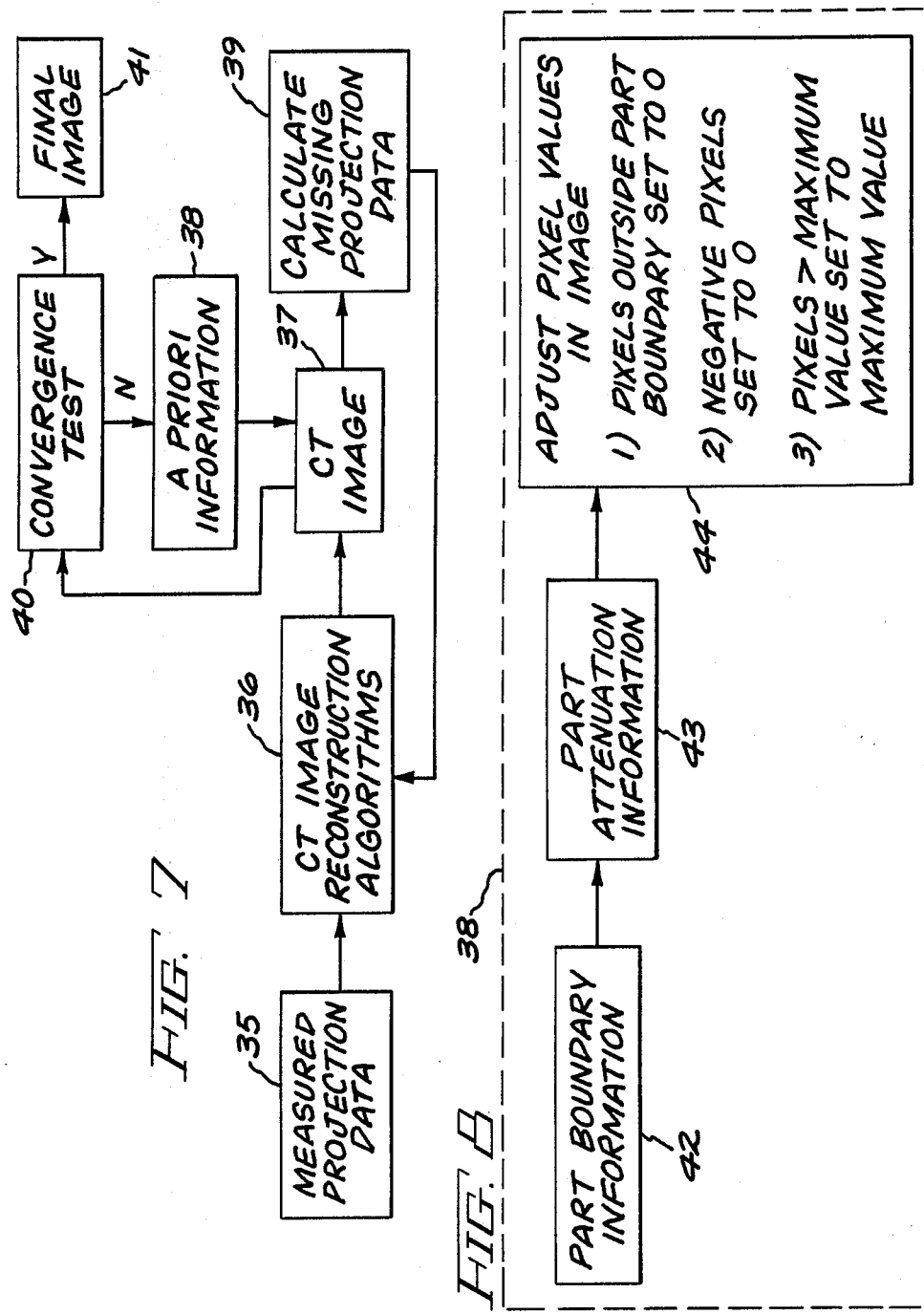

ENHANCEMENT OF IMAGE QUALITY BY UTILIZATION OF A PRIORI INFORMATION

BACKGROUND OF THE INVENTION

This invention relates to a method of improving the quality of non-destructive examination (NDE) images, and more particularly to incorporating a priori information into incomplete data NDE images.

Good image quality and substantial information about a part are provided when the images are based on a complete data set, for instance that there are sufficient spatial an angular samples to create an image consistent with part and flaw geometry. However, complete data for image reconstruction is not always available. Consider X-ray CT (Computerized Tomography) as an example. In certain cases it may be impossible to manipulate a part in such a way that data can be taken at all the required view angles around the part. In other cases, the part may attenuate x-rays too much to allow penetration in some directions or at some locations. In FIG. 1, where the x-ray source and detector are shown at 10 and 11, sections of part 12 obstruct the data acquisition scan over a portion of the angular range; even if a horizontal scan is made the x-ay path length through the part is too great to allow sufficient x-ray penetration for meaningful measurement. Incomplete data is the result, and incomplete data images generally show serious artifacts that limit the ability to properly inspect the part and detect flaws.

Previous techniques for dealing with this problem include attempts to extract relevant flaw information directly from the image with artifacts, and attempts to incorporate certain part information in an iterative fashion. The latter may include non-negativity of the pixels in an image, maximum value of the pixels in the image, and rough shape information; see U.S. Pat. No. 4,506,327—Tam and "Tomographical Imaging with LimitedAngle Input", K. C. Tam and V. Perez-Mendēz, J. Opt. Soc. Am., Vol. 71 (1981), pp. 582-592. The a priori information which is available and the techniques for using it have generally been quite limited.

SUMMARY OF THE INVENTION

An object of the invention is to effectively incorporate significant amounts of a priori information into the image reconstruction and image processing to supplement the information in the available measured data.

. Another object is provide improved NDE images in those situations where incomplete data is available by incorporating more precise a priori information such as the accurate knowledge of part geometry provided by solid modeling systems.

There are several sources of a priori information which can be utilized. First, a CAD (Computer-Aided Design) electronic model of a part; a solid modeler that yields an accurate three-dimensional model is chosen. Second, the physics and geometry of the inspection process are known and the physical properties of the part and imaging agent source. Third, other sensor readings acquired during part inspection, such as boundary information from a touch sensor, can provide additional a priori information. An advantage of the electronic model is that such solid models provide interior as well as exterior boundary information.

The invention is applicable to many NDE imaging techniques and modalities, including but not limited to x-ray imaging, digital radiography, ultrasonic inspection, eddy current inspection, and infrared and visual inspection.

One aspect of the invention is a method of NDE imaging utilizing improved a priori information comprisiing the steps of: scanning a part with an imaging agent over an available range and generating measured imaging parameter data; providing a three-dimensional model of the part and calculating relevant part geometry, and providing selected physical properties of the part and possibly the imaging agent source; combining the part geometry and physical properties and calculating imaging parameter data over an unavailable scanning range that cannot be scanned because of physical or operational constraints; and forming an image of the part from the measured and calculated imaging parameter data.

The preferred embodiments of the invention are three approaches at improving the quality of limited angle x-ray CT images with more accurate a priori information. The projection data approach is a method comprising scanning a part with x-rays over a limited angular range and generating measured projection data at available view angles; providing an electronic model of the part which is derived from a three-dimensional solid modeler and calculating x-ray attenuation from known physical parameters of the part and x-ray source; calculating projection data at the missing view angles from the path lengths and attenuation; and reconstructing an image of the part from the measured and calculated projection data which together provide a complete data set for CT reconstruction algorithms. Another feature is that the calculation of path lengths through the electronic model comprises an intermediate step of converting part geometry from the solid model to a two-dimensional pixel image from which path lengths are calculated.

The image processing and analysis method is: scanning with x-rays over the available limited angular range and reconstructing a partial image from measured projection data; calculating model projection data at a complete set of view angles by calculating path lengths through the electronic model and x-ray attenuation as just described; reconstructing a model partial image from model projection data over the same angular range as the measured data, a model full image from complete model projection data, and subtracting the model full and partial images to provide a model difference image representing a limited angle reconstruction error; and combining the partial image reconstructed from measured data and model difference image to yield a final image.

The iterative reconstruction method comprises scanning with x-rays over the available limited angular range and reconstructing an image from measured data; calculating accurate part boundary information from a model of the part, and x-ray attenuation from known physical parameters; adjusting the image with this a priori information by setting pixels outside of the part boundary to zero, negative pixels to zero, and pixels greater than a preselected value of attenuation to the maximum value; calculating from the modified image the missing projection data at missing view angles; reconstructing a new image from the measured projection data and calculated missing projection data; and iterating as required until sufficient image quality is attained.

BRIEF DESCRIPTION OF THE DRAWINGS

FIG. 1 illustrates an object with protrusions making it impossible to carry out complete angle scanning.

FIG. 2 is a block diagram of a generic technique of incorporating significant and more accurate a priori information about an object into the image formation process.

FIGS. 3a and 3b show characteristic features of images of a vertical cross section through a jet engine part reconstructed with complete data and incomplete data.

FIG. 4 illustrates x-ray CT inspection of the part and the measured projections derived from a limited angle data set and missing projections calculated from a priori information according to the invention.

FIG. 5 is a block diagram of the projection data approach to utilize a priori information and improve the quality of NDE images.

FIG. 6 shows the steps to calculate missing projection data needed in the foregoing.

FIG. 7 is a block diagram of the iterative reconstruction approach.

FIG. 8 shows the steps in calculating and utilizing a priori information according to the iterative reconstruction technique.

DETAILED DESCRIPTION OF THE INVENTION

Figure 9:
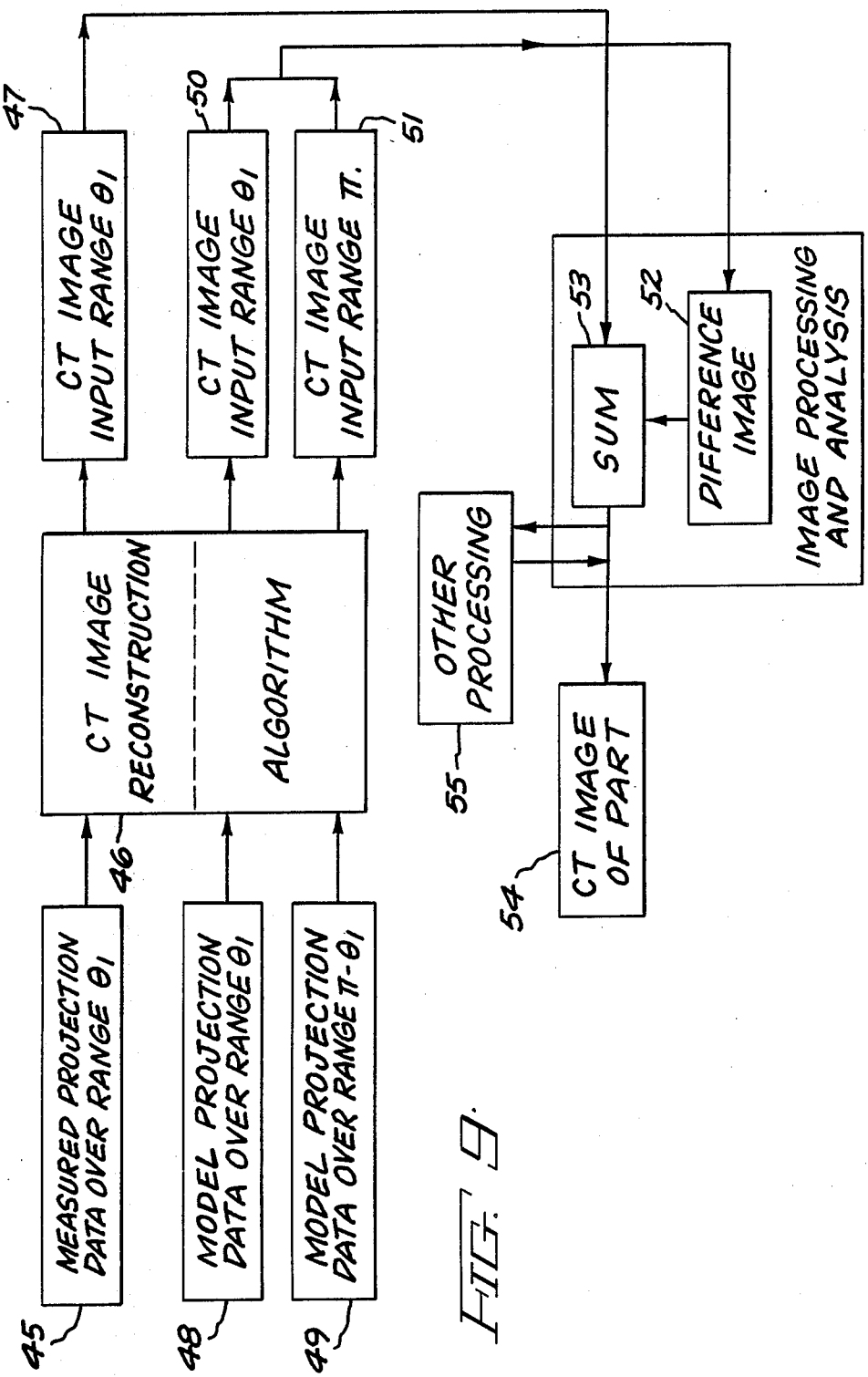
FIG. 9 is a block diagram of the image analysis and processing approach to reconstructing CT images.

Two methods of improving the quality of incomplete data NDE images by incorporating a priori information are shown in FIG. 2. Referring to blocks 13-16, the available experimental data is combined with the a priori information by the image formation algorithm to yield an intermediate image. The required a priori information is obtained from two sources, blocks 17 and 18, knowledge of the part geometry from models of the part or from sensors, and physical parameters of the part and possibly imaging agent source derived from knowledge of the physics of the inspection process. The intermediate image may or may not have sufficient quality for the intended purpose. The intermediate image could be noisy or contain artifacts due to incomplete data, for example. The a priori information, blocks 19-21, is utilized by an image processing algorithm to enhance the final image quality. The material properties of the part and its flaw properties are determined from the final image. For instance, a steel object may be inspected to see if it has rust spots and voids in the metal. Accept and reject decisions are made based on what is found in the final image, either by an operator or an algorithm. The a priori information may be utilized in both the image formation and image processing or at only one point.

A typical large part of interest for X-ray CT inspection is an exhaust nozzle actuation ring from an aircraft engine. A complex vertical cross section through the actuator ring is shown at 22 in FIG. 3a, and is the section through one of the bosses which extends above the top wall in five locations in the part. This part has a multi-wall structure which is difficult to inspect using conventional NDE techniques. The optimum inspection configuration is to create CT slices through each wall section of the part, such that the CT slice is parallel to the part symmetry axis. A reconstructed CT image with complete data would be as shown in FIG. 3a. For parallel beam data, a 180° scan provides complete data. An image of the same section showing characteristic features of a CT image with incomplete data is shown at 23 in FIG. 3b. The missing data is in a 40° cone, out of 180°, parallel to the long axis of the part 22 as is seen in FIG. 4. The part cross section is considerably higher than it is wide, and due to the relatively high aspect ratio of the section, x-ray penetration in the long path length direction is a problem. Particularly noticeable is the lack of information about walls parallel to the missing data directions, and it was found that artifacts are present throughout the image. It is clear that part quality is extremely difficult to assess based on such limited angle images. The methods of this invention of incorporating significant amounts of accurate a priori information into the incomplete data NDE image yields a high quality image comparable to a complete data image.

A CAD electronic model, a solid model of the part derived from a three-dimensional solid modeler, is an excellent source of part geometry information. Use is made of effectively all the information which is made available in the blueprint of a selected industrial part. An electronic model is simply a mathematical representation of the geometry of a part, stored in a format which is practical for computer use. The specific mathematical representation determines the accuracy of the object model: simple wire frame models, which are unacceptable for this application, may be created by points and the arcs that connect them, while solid models may be created from surfaces which, in turn, are created from curves and points. An accurate solid model may be rotated and sectioned to provide information about what the object would look like under specific conditions, information which is not normally available without destroying the object. The preferred solid modeling system is General Electric's TRUCE solid modeler; it is described in "TRUCE—The Tridimensional Rational Unified Cubic Engine—User's Guide", R. T. Farouki and J. R. Hinds (1985), General Electric Co., Corporate Research and Development, P.O. Box 8, Schenectady, N.Y. 12301. Reference may also be made to U.S. Pat. No. 4,618,924—Hinds. Other solid modeling systems may be employed but should have sufficient accuracy for real manufacturing. The solid model provides precise internal part boundary information as well as exterior boundary information.

Another source of a priori information is the physics of the inspection process. By way of illustration, the x-ray physics and geometry of the inspection effectively determine the x-ray absorptivity of the part, which is the imaged parameter in X-ray CT.

Part geometry information may be provided by a touch sensor and other supplemental sensor readings acquired during part inspection. Such a sensor provides part location information and additional information about how much a manufactured part differs from the electronic model. If the part is relatively simple and can be completely scanned by the touch sensor, this may be the sole source of the additional a priori information on the exterior boundary of the part.

Several techniques have been developed for incorporating model information into limited angle CT images to improve image quality. Three approaches for incorporating a priori information are discussed, the projection data approach, the iterative reconstruction approach, and the image analysis and processing approach. The basic concept is illustrated in FIG. 4 where the measured projections 24 at available view angles over the limited angular range are combined with synthesized missing projections 25 from the model at missing view angles over the unavailable scanning range, to improve the quality of the CT image.

The projection data approach, FIG. 5, blocks 26-29, comprises acquiring measured projection data over the available angular range, calculating projection data from the solid model over the missing angular range, and reconstructing the CT image from measured projection data in the available angular range and calculated projection data in the missing angular range. The measured and calculated projection data together provide a complete data set for CT image reconstruction algorithms. The final part image has excellent image quality. The steps in calculating missing projection data using the part geometry from the solid modeler and known physical parameters of the part and x-ray source are shown in FIG. 6 at 30-34. A section through the three-dimensional solid model is converted to a two-dimensional pixel image and path lengths that would be taken by x-rays are calculated. When the x-ray detector is an array, there may be a large number of path lengths to calculate, from the source focal spot to every detector element. Path lengths in the part in the missing angular range may be computed using the Donner Algorithms for Reconstruction Tomography, R. H. Huseman et al, Lawrence Berkeley Laboratory, University of California (1977). The Donner package provides the basic CT reconstruction function also. The x-ray attenuation by the part depends on the path length, material of the part, and x-ray energy. The material is given on the blueprint, and if a metal alloy the constituents of the alloy are known. A convenient method of calculation is to use the average energy out of the x-ray tube. Published tables list an attenuation coefficient for each element of the alloy, and these are mixed according to a given formula. Multiplying the path length by the coefficient yields the projection data. A more exact calculation is to use tables that apply to all energies in the x-ray tube; the input is the path length and attenuation is computed directly.

The iterative reconstruction approach, FIGS. 7 and 8, is based on a method given in the previously referenced published paper by Tam and Perez-Medez, but utilizes significantly improved a priori information. An x-ray scan of the part is performed over the available limited angular range and measured projection data is acquired. Referring to blocks 35-37, a real partial image of a part is reconstructed from the available projection data, using filtered backprojection or another algorithm. In this approach the reconstructed image is transformed back and forth between the object space by filtered backprojection, and the projection space by projection, being repeatedly corrected by the a priori information about the object in the object space and by the known projections in the projection space. Three types of a priori information, blocks 38 and 42-44, are applied to the limited angle image. A model of the part is provided and part boundary information is calculated. The electronic model derived from a solid modeling system supplies precise exterior boundary information and, if the part such as that in FIG. 3a is partly hollow, accurate interior boundary information as well. Alternatively, the three-dimensional shell provided by a touch sensor may be used, but this gives only exterior boundary information. Another alternative is determine the convex hull of the part as explained in copending application Ser. No. 232,804, filed Apr. 1, 1987, K. C. Tam; this yields only exterior boundary information.

Part attenuation is calculated as already described, by calculating the path length through the part, the attenuation coefficient given the material of the part and x-ray source energy, and multiplying these two parameters.

Pixel values in the real partial CT image 37 are adjusted by, first, setting to zero pixels outside the part boundary. Where the part boundary information is obtained from an electronic model, the exterior and interior boundaries are both known to a high degree of accuracy. Second, negative pixels are set to zero. Third, pixels greater than some chosen maximum value of attenuation are set to the maximum value. The maximum may be, for instance, the calculated attenuation or twice that value. The missing projection data, block 39, in angles outside of the limited angular range are calculated from the resulting modified image. A new image is then reconstructed from the measured projection data in the available angular range and the calculated projection data from the modified CT image in the missing angular range. The foregoing procedure is iterated as required. A series of progressively improved images 37 are reconstructed until sufficient image quality is attained. The iterative reconstructions are shown to converge, and a suitable convergence test, block 40, determines if another iteration is needed or if the quality is sufficient to output the final image 41.

The image processing and analysis method, FIG. 9, is related to the projection approach but has the advantage of allowing off-line processing of the error correcting image, and easy access to data at different points than in the projection data approach. The diagram is for parallel beam data where a 180° scan provides complete data. The part is scanned with x-rays over the limited angular range $\theta_1$, blocks 45-47, and measured projection data is acquired at the available view angles. Applying the filtered backprojection reconstruction algorithm, a real partial image of the part is reconstructed from the available measured data. Model projection data at a complete set of view angles is calculated, blocks 48 and 49. In the same manner as before, an electronic model of the part is provided, and path lengths through the part are calculated at both the available view angles over the range $\theta_1$ and the missing view angles over the range $\pi - \theta_1$. Attenuation coefficients are calculated from the known physical parameters of the part and x-ray source, and path length is multiplied by the attenuation coefficient. A model real partial CT image 50 is reconstructed from the model projection data over the same angular range as the measured projection data. A model full CT image 51 is reconstructed from the complete model projection data over the input range $\pi$. A model difference image, block 52, is constructed by subtraction and normalization of the model full and real partial images. The difference image, representing the limited angle reconstruction error, is then combined or summed at 53 with the partial image reconstructed from measured projection data to arrive at the best CT image 54 of the part. As shown as 55, other image processing may be performed at this stage.

Three techniques and methods of improving the quality of NDE images by incorporating more accurate a priori information have been discussed. Which method is selected depends on the type of flaw information sought. The iterative reconstruction approach, while computationally intensive, is best to inspect for voids because there is high contrast with the base material to start with. A microshrink on the other hand is close to the background with only a 5-10% difference, and the projection data approach is best because it eliminates artifacts. It was found that some parts that were previously uninspectable by the usual NDE techniques are now inspectable using these methods.

The invention can be used in almost any NDE imaging technique, including but not limited to x-ray computed tomography, digital radiography, ultrasonsic inspection (B-scan, C-scan, etc.), eddy current inspection, infrared and visual inspection, and others. In each of these imaging modalities there may be a reason as to why only incomplete data can be acquired. The reason why complete data cannot be measured will be apparent. The method of NDE imaging by incorporating a priori information is summarized as follows. A part is scanned with an imaging agent (x-rays, ultrasound, infrared radiation, etc.) over the available scanning range and measured imaging parameter data is generated. From a three-dimensional model of the part the relevant part geometry is calculated. Selected physical parameters and properties of the part and imaging agent source are known. The part geometry information and physical properties are combined to determine calculated imaging parameter data over an unavailable scanning range that cannot be scanned due to a constraint. An image of the part is then formed from the combined measured and calculated data. Further information and simulation results using a CAD model of the actuation ring part are given by the inventors in their technical paper "Use of a Priori Information in Incomplete Data X-ray CT Imaging", Review of Progress in Quantitative Nondestructive Evaluation, Vol. 7.

While the invention has been particularly shown and described with reference to preferred embodiments thereof, it will be apparent to those skilled in the art that the foregoing and other changes in form and details may be made without departing from the spirit and scope of the invention as defined in the appended claims.

The invention claimed is:

1. A method of NDE (non-destructive evaluation) imaging by incorporating a priori information comprising:
   scanning a part with an imaging agent over an available scanning range an generating measured imaging parameter data;
   providing a three-dimensional model of said part and calculating relevant part geometry, and providing selected physical properties of said part and said imaging agent;
   combining said part geometry and physical properties and determining calculated imaging parameter data over an unavailable scanning range that cannot be scanned due to a constraint by calculating imaging agent path lengths through said model and calculating attenuation of said imaging agent from said physical properties; and
   forming an image of said part from said measured and calculated data.

2. The method of claim 1 wherein said imaging agent is x-rays.

3. The method of claim 1 wherein said model is an electronic model derived from a solid modeling system.

4. A method of NDE (non-destructive evaluation) imaging utilizing improved a priori information comprising:
   scanning a part with an imaging agent over a limited angular range and generating measured projection data at available view angles;
   providing an electronic model of said part which is derived from a three-dimensional solid modeler, and calculating imaging agent path lengths through said model at missing view angles;
   calculating attenuation of said imaging agent by said part from known part materials and x-ray source energy;
   determining calculated projection data at said missing view angles from said path lengths and attenuation; and
   reconstructing an image of said part from said measured and calculated projection data.

5. The method of claim 4 wherein said imaging agent is x-rays.

6. The method of claim 4 wherein said calculating path length through said model comprises an intermediate step of converting part geometry from said electronic model to a two-dimensional image from which said path lengths are calculated.

7. A method of NDE (non-destructive evaluation) imaging utilizing improved a priori information comprising:
   scanning a part with x-rays over a limited angular range and generating measured protection data at available view angles;
   providing an electronic model of said part which is derived from a three-dimensional solid modeler and calculating x-ray path lengths through said electronic model at missing view angles;
   calculating attenuation from known physical parameters of said part and an x-ray source;
   determining calculated projection data at the missing view angles from said path lengths and attenuation; and
   reconstructing an image of said part from said measured and calculated projection data which together provide a complete data set for computed tomography reconstruction algorithms.

8. The method of claim 7 wherein said calculating path lengths through said electronic model comprises an intermediate step of converting part geometry from said solid modeler to a two-dimensional pixel image from which said path lengths are calculated.

9. A method of NDE (non-destructive evaluation) imaging utilizing improved a priori information comprising:
   scanning a part with x-rays over a limited angular range and generating measured projection data at available view angles;
   reconstructing a partial image of said part from said measured projection data;
   providing an electronic model of said part which is derived from a three-dimensional solid modeler and calculating path lengths through said model at both available and missing view angles, attenuation from known physical parameters of said part and x-ray source, and model projection data at a complete set of view angles;
   reconstructing a model partial image from said model projection data over the same angular range as said measured data, and a model full image from complete model projection data, and subtracting said model full and partial images to provide a model difference image representing a limited angle reconstruction error; and
   combining said partial image reconstructed from measured data and said model difference image to yield a final part image.

10. The method of claim 9 wherein said calculating path lengths through said electronic model comprises an intermediate step of converting part geometry from said solid modeler to a two-dimensional pixel image from which said path lengths are calculated.

* * * * *